United States Patent
Gaillot et al.

(10) Patent No.: US 10,912,890 B2
(45) Date of Patent: *Feb. 9, 2021

(54) MEDICAL DELIVERY DEVICE

(71) Applicant: HOFFMANN-LA ROCHE INC., Little Falls, NJ (US)

(72) Inventors: Maxime Gaillot, Basel (CH); Roberta Leah, Basel (CH); Declan Reilly, Basel (CH); Mark Digby Teucher, Bath (GB); Paul Graham Hayton, Bristol (GB); Jonathan Paul Ridley, Bristol (GB); James Robert Coop, Bristol (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/062,014

(22) PCT Filed: Dec. 13, 2016

(86) PCT No.: PCT/EP2016/080833
§ 371 (c)(1),
(2) Date: Jun. 13, 2018

(87) PCT Pub. No.: WO2017/102751
PCT Pub. Date: Jun. 22, 2017

(65) Prior Publication Data
US 2018/0369493 A1 Dec. 27, 2018

(30) Foreign Application Priority Data

Dec. 14, 2015 (EP) .................................... 15199909
Dec. 14, 2015 (EP) .................................... 15199911
(Continued)

(51) Int. Cl.
*A61M 5/20* (2006.01)
*A61M 5/315* (2006.01)
(Continued)

(52) U.S. Cl.
CPC ................ *A61M 5/204* (2013.01); *A61J 1/20* (2013.01); *A61J 1/2006* (2015.05); *A61J 1/2096* (2013.01);
(Continued)

(58) Field of Classification Search
CPC .............. A61M 5/204; A61M 5/31571; A61M 5/3213; A61M 5/31561; A61M 5/3158;
(Continued)

(56) References Cited

U.S. PATENT DOCUMENTS

| 4,312,343 A | 1/1982 | Leveen et al. |
| 4,583,978 A * | 4/1986 | Porat .................. A61M 5/31511 604/208 |

(Continued)

FOREIGN PATENT DOCUMENTS

| JP | S56-028770 A | 3/1981 |
| JP | 2003-527933 A | 9/2003 |

(Continued)

OTHER PUBLICATIONS

International Search Report dated Mar. 28, 2017 in corresponding International Patent Application No. PCT/EP2016/080833.
(Continued)

*Primary Examiner* — Laura A Bouchelle
*Assistant Examiner* — Anh Bui
(74) *Attorney, Agent, or Firm* — Medler Ferro Woodhouse & Mills PLLC (57) ABSTRACT

A medical delivery device is disclosed having a rod element with a stem and a first thread arrangement, a dial shell with a second thread arrangement, a delivery orifice, and a
(Continued)

switching mechanism. In a dosing status, the rod element is movable relative to the delivery orifice by rotating the dial shell around the stem causing the first thread arrangement and the second thread arrangement to travel along each other, a dosage chamber is formed between the rod element and the delivery orifice when the rod element moves away from the delivery orifice, and the rod element is prevented from movement along a longitudinal axis when an axial force is applied. In a delivery status, the rod element is movable along the longitudinal axis relative to the delivery orifice when an axial force is applied and moving the rod element by rotating the dial shell around the stem is prevented.

15 Claims, 7 Drawing Sheets

(30) Foreign Application Priority Data

| Dec. 14, 2015 | (EP) | 15199913 |
|---|---|---|
| Dec. 14, 2015 | (EP) | 15199915 |
| May 3, 2016 | (EP) | 16167999 |

(51) Int. Cl.
  *A61M 5/178* (2006.01)
  *A61J 1/20* (2006.01)
  *A61M 5/32* (2006.01)
  *A61M 5/24* (2006.01)
  *A61M 5/31* (2006.01)

(52) U.S. Cl.
  CPC ............ *A61M 5/1782* (2013.01); *A61M 5/20* (2013.01); *A61M 5/2422* (2013.01); *A61M 5/3146* (2013.01); *A61M 5/3158* (2013.01); *A61M 5/31505* (2013.01); *A61M 5/31525* (2013.01); *A61M 5/31528* (2013.01); *A61M 5/31536* (2013.01); *A61M 5/31551* (2013.01); *A61M 5/31553* (2013.01); *A61M 5/31561* (2013.01); *A61M 5/31571* (2013.01); *A61M 5/3213* (2013.01); *A61M 2005/3126* (2013.01); *A61M 2205/58* (2013.01); *A61M 2205/581* (2013.01); *A61M 2205/582* (2013.01); *A61M 2205/583* (2013.01)

(58) Field of Classification Search
  CPC ............... A61M 5/31536; A61M 5/20; A61M 5/31551; A61M 5/31505; A61M 5/3146; A61M 5/2422; A61M 5/1782; A61M 5/3153; A61M 5/31528; A61M 5/31525; A61M 2205/58; A61M 2205/582; A61M 2205/581; A61M 2205/583; A61M 2005/3126; A61J 1/2006; A61J 1/2096; A61J 1/20
  See application file for complete search history.

(56) References Cited

U.S. PATENT DOCUMENTS

| 4,810,249 | A | 3/1989 | Haber et al. |
|---|---|---|---|
| 6,607,508 | B2 | 8/2003 | Knauer |
| 2001/0037087 | A1* | 11/2001 | Knauer ................. A61M 5/204 604/137 |
| 2003/0105430 | A1 | 6/2003 | Lavi et al. |
| 2011/0034870 | A1 | 2/2011 | Glejboel et al. |

FOREIGN PATENT DOCUMENTS

| JP | 2010-527248 A | 8/2010 |
|---|---|---|
| JP | 2012-528639 A | 11/2012 |
| JP | 2013-507214 A | 3/2013 |
| JP | 2014-527894 A | 10/2014 |
| JP | 2015-526218 A | 9/2015 |
| JP | 2016-530018 A | 9/2016 |
| JP | 2018-537209 A | 12/2018 |
| JP | 2019-502442 A | 1/2019 |
| WO | 01/52920 A2 | 7/2001 |
| WO | 2008/093063 A2 | 8/2008 |
| WO | 2008/119691 A2 | 10/2008 |
| WO | 2010/139671 A1 | 12/2010 |
| WO | 2011/095488 A1 | 8/2011 |
| WO | 2012/143437 A1 | 10/2012 |
| WO | 2017/102760 A1 | 6/2017 |

OTHER PUBLICATIONS

Written Opinion dated Mar. 28, 2017 in corresponding International Patent Application No. PCT/EP2016/080833.
Notice of Reasons for Rejection dated Dec. 1, 2020 in corresponding Japanese Patent Application No. 2018-530746.
Search Report dated Nov. 10, 2020 in corresponding Japanese Patent Application No. 2018-530746.
Notice of Reasons for Rejection dated Dec. 1, 2020 in corresponding Japanese Patent Application No. 2018-530680.
Search Report dated Nov. 10, 2020 in corresponding Japanese Patent Application No. 2018-530680.
Notice of Reasons for Rejection dated Dec. 1, 2020 in corresponding Japanese Patent Application No. 2018-530752.
Search Report dated Nov. 10, 2020 in corresponding Japanese Patent Application No. 2018-530752.
Notice of Reasons for Rejection dated Nov. 13, 2020 in corresponding Japanese Patent Application No. 2018-530751.
Search Report dated Nov. 6, 2020 in corresponding Japanese Patent Application No. 2018-530751.

* cited by examiner

MEDICAL DELIVERY DEVICE

TECHNICAL FIELD

The present invention relates to a medical delivery device according to the preamble of independent claim 1. Such a device can be embodied by the following components: (i) a rod element having a stem with a longitudinal axis, a first thread arrangement, a proximal end and a distal end; (ii) a dial shell having a second thread arrangement; and (iii) a delivery orifice arranged adjacent to the proximal end of the rod element. In a dosing status of the medical delivery device, the first thread arrangement of the rod element and the second thread arrangement of the dial shell engage. The rod element is movable along the longitudinal axis of its stem relative to the delivery orifice by rotating the dial shell around the stem of the rod element causing the first thread arrangement of the rod element and the second thread arrangement of the dial shell to travel along each other, wherein a dosage chamber is formed between the rod element and the delivery orifice when the rod element is moved away from the delivery orifice. Devices of this kind can be used by a patient self-administering a liquid such as a medicament or a drug.

BACKGROUND ART

Delivering a liquid or other fluid out of a container is required in many medical applications and performed in a plurality of different ways. Particularly where it is essential that the liquid is comparably precisely provided, specific devices are commonly used. For example, liquid pharmaceutical substances are often provided in glass or plastic vials or containers which are closed by a septum or rubber plug and a metal cap clamped around it or another similar seal cover.

Conventionally, for delivering the pharmaceutical substance out of vials, syringes are used. Thereby, a needle attached to the syringe penetrates the septum or cover and the pharmaceutical substance is withdrawn into the syringe through the needle. Once transferred into the syringe, the pharmaceutical substance is delivered in an appropriate manner. For example, the pharmaceutical substance can be, e.g. subcutaneously or intramuscularly, injected from the needle into a patient or it can be orally applied or provided as droplets, e.g., in the eyes or nose of the patient.

Delivering liquids from vials or containers by means of syringes usually is comparably difficult. This typically makes it necessary that an educated person such as a doctor or a nurse is involved. In particular, in cases where the dosage of liquid delivered has to be comparably precise such as when comparable small volumes such as in a range of ten microliter to about one milliliter are involved patients are typically not capable of performing the delivery themselves when using a regular syringe or a similar device, i.e. self-administration is not possible. However, self-administration of liquids or medicaments is beneficial in many therapeutic applications since the effort for the patient and the costs of the therapy can be extensively reduced.

For improving this situation, there are devices used which allow for more conveniently delivering a comparably precise volume of liquids. For example, it is known to provide medicaments in prefilled syringes which can be administered by the patients themselves. However, such prefilled syringes are often not preferred for plural reasons.

For example, producing prefilled syringes is comparably complicated and expensive compared to vials in terms of manufacturing. Other examples of delivery devices are injection pens which are often used in the therapy of diabetes.

Further, U.S. Pat. No. 6,607,508 B2 describes an automatic medicament delivery device having a cylindrical syringe barrel into which a plunger rod extends from one side. The other side of the syringe barrel is equipped with a thread onto which a needle assembly can be screwed. The plunger rod has a vial seat into which a vial can be snapped in. The plunger rod is further equipped with a pathway longitudinally extending throughout the entire plunger rod. Radially from the plunger rod pins extend which interengage with slots of a dose barrel surrounding the section of the plunger rod having the pins. By turning the dose barrel via a dose ring the plunger rod translates and a volume is created between the plunger rod and the thread side of the syringe barrel. Induced by this movement a medicament is transferred from the vial through the pathway into the volume. The turning of the dose barrel into an opposite direction is blocked by a ratchet mechanism which ensures that no liquid can be pressed back through the pathway. The device further has a spring driven and automatic needle injecting arrangement for delivering the medicament from the volume through a needle screwed to the thread of the syringe barrel. During medicament delivery the plunger rod is automatically turned in the opposite direction by a spring force and the volume is reduced. Thereby, the medicament is pressed trough the needle.

Even though such known delivery devices are improving the situation with respect to a convenient handling and feasibility of self-administration, they still are comparably complicated to use particularly for precisely dosing and for administering the liquid after dosing. Also, when using rotatable dosing or delivery devices, delivery of the liquid can be rather slow which makes the administration comparably cumbersome.

Therefore, there is a need for a medical delivery device allowing on one hand for a precise dosing of a liquid out of a container and on the other hand for a convenient dosing and self-administration of the liquid.

DISCLOSURE OF THE INVENTION

According to the invention this need is settled by a medical delivery device as it is defined by the features of independent claim 1. Preferred embodiments are subject of the dependent claims.

In particular, the invention deals with a medical delivery device comprising, a rod element, a dial shell, a delivery orifice and optionally a housing. The housing has an interior, a proximal opening and a distal opening. The rod element optionally extends into the interior of the housing. It has a stem with a longitudinal axis, a first thread arrangement, a proximal end and a distal end. The dial shell optionally extends into the interior of the housing and has a second thread arrangement. The delivery orifice is arranged adjacent to the proximal end of the stem of the rod element. In a dosing status of the medical delivery device, the first thread arrangement of the rod element and the second thread arrangement of the dial shell engage. Further, in the dosing status of the medical delivery device, the rod element is movable along the longitudinal axis of its stem relative to the delivery orifice by rotating the dial shell around the stem of the rod element causing the first thread arrangement of the rod element and the second thread arrangement of the dial shell to travel along each other, wherein a dosage chamber is formed optionally in the interior of the housing between the rod element and the delivery orifice which increases when the rod element is moved away from the delivery orifice.

The medical delivery device further comprises a switching mechanism for changing the medical delivery device from the dosing status to a delivery status. In the dosing status of the medical delivery device moving the rod element along the longitudinal axis of its stem by applying an axial force to the rod element is prevented. In the delivery status of the medical delivery device, the rod element is movable along the longitudinal axis of its stem relative to the delivery orifice by applying an axial force to the rod element and moving the rod element along the longitudinal axis of its stem by rotating the dial shell around the stem of the rod element is prevented.

The term "proximal" as used in connection with the invention and the disclosed embodiments thereof can relate to an orientation of the medical delivery device which in its intended use is directed to a body of the patient. Thereby, proximal portions or parts can be directed to or positioned closer to the body of the patient when the medical delivery device is applied to the patient. Contrary, the term "distal" as used in connection with the invention and the disclosed embodiments thereof can relate to an orientation of the medical delivery device which in its intended use is directed away from the body of the patient. For example, in a conventional syringe the proximal end usually is the tip of the needle and the distal end is the end of the plunger where the thumb is to be laid.

The term "thread" as used herein relates to a male structure such as a ridge or a female structure such as a groove extending along and around a surface or body. Typically threads are helically or essentially helically shaped and run along and around a body or part.

The optional housing can be more or less cylindrically shaped. It can also comprise a cap such as a needle shield. The distal and proximal openings can be embodied at respective distal and proximal end sides of the housing. It can have a flange portion as finger rest at or near its distal end in which the distal opening is arranged. The housing can particularly form an outer envelope of the medical delivery device. It can be shaped to allow a convenient handling and use of the device as well as to protect the components in its interior.

The term "extend into" in connection with the rod element, the dial shell, the housing and other parts can relate to being fully or partially arranged inside. It can, for example, relate to an arrangement where a portion of a part is partially outside another part but projects into the other part.

The first thread arrangement can be an outer thread arrangement and, correspondingly, the second thread arrangement can be an inner thread arrangement. The term "outer" in connection with the thread arrangement can relate to a direction into which the thread arrangement is oriented. In particular, it can relate to a thread arrangement being outwardly oriented such that it can interact with a corresponding inner thread arrangement. Similarly, the term "inner" in connection with the thread arrangement can relate to an opposite direction into which the thread arrangement is oriented.

The stem of the rod element can have the shape of a post or cylinder. While extending into the interior of the housing the distal end of the body of the rod element can lie close to the distal end of the housing and the proximal end of the stem of the rod element can lie close to the proximal end of the housing.

The dial shell can be arranged at least partially around the rod element or at least around its section where the first thread arrangement is located. It can be embodied as a hollow cylinder or it can comprise one or plural cylinder segments which, for example, together can form a hollow cylinder. In particular, it can consist of two essentially half-cylindrical walls or clamshells.

Rotating the shell and the rod element relative to each other can be embodied by either the dial shell rotating around the rod element, the rod element rotating in the dial shell or the dial shell and the rod element both rotating. For an efficient appropriate rotational movement the dial shell and the rod element can be coaxially arranged.

The term "travel along each other" as used in connection with the first and second thread arrangements can relate to a part being moved or shifted in or on the thread. For example, a male member such as a pin can be moved in and along a groove of a female thread.

The delivery orifice can be shaped for a particular application or administration of a medicament to be delivered from the device. For example, it can be a needle if the device is intended for injecting the medicament. In such an embodiment the delivery orifice or needle can extend from the interior of the housing through its proximal opening out of the housing or a specific part thereof. The delivery orifice can also be adapted for being connected to a delivery member. For example, it can comprise a male or female part of a Luer lock or Luer taper connector and the delivery member can be equipped with a corresponding female or male Luer lock connector. Other examples of delivery orifices are nozzles, valves, fluid guides or the like.

The term "axial force" as used in connection with moving the rod element, when the medical delivery device is in the delivery status, can relate to a force applied to the rod element in order to axially move it. Typically such axial force can be manually induced, e.g. by pushing with a thumb on the distal end of the rod element or on a container mounted to the rod element or on another part connected to the rod element.

In this connection the term "prevent" can relate to impeding the axial force to axially move the rod element. It is understood that if the axial force is high enough the rod element could still be axially moved, e.g., by breaking certain parts of the device. Thus, preventing the axial movement by an axial force can relate to a proper use of the device.

The term "container" as used herein can relate to any liquid reservoir suitable for storing and transporting a liquid. Where the liquids are medicaments or the like, the container can particularly be a vial. The term "vial" as used in this connection can relate a comparably small vessel or bottle, commonly used to store pharmaceutical products or pharmaceuticals or medicaments in liquid, powdered or capsuled form. The vial can be made of a sterilisable material such as glass or plastic such as, e.g., polypropylene.

The medical delivery device can be made of a plastic material. In particular, it can be made of a sterilisable plastic material which can be manufactured in an injection molding process.

By providing the medical delivery device with the switching mechanism, in use, it can be clearly distinguished between the dosing status and the delivery status. This allows for functionally separating the dosing of a liquid such as a medicament from the delivery of the liquid. Typically, in a first step the medical delivery device is in the dosing status. In this status, the liquid can be precisely dosed into the dosage chamber by rotating the dosing shell. Any unintended activation of the medical delivery device, e.g. by applying an axial force to the rod element, which would impair the accuracy of the dosing can thereby be prevented. This makes a precise and safe dosing of the liquid conveniently possible and assures that the liquid is not administered until the dosing is finished.

After switching the medical delivery device into the delivery status, further dosing is prevented which allows for hindering an impairing of the precise delivery of the liquid. Also, in the delivery status, activation of the medical delivery device can be particularly convenient since no further dosing is possible and accordingly no measures have to be taken to prevent unintendedly changing dosage during administration. This makes self-administration of the liquid particularly convenient and safe. Also, since a straight or axial activation is possible, delivery can be comparably fast. The switching mechanism can be embodied that it is not possible to switch the medical delivery device back to the dosing status once it is in the delivery status. Also, the switching mechanism can be arranged to be only active or activated after a predefined volume is dosed or after the dial shell is rotated to a predefined extent.

Thus, the medical delivery device according to the invention allows for on one hand to precisely dosing a liquid, for example from a container, and on the other hand for a convenient self-administration of the liquid after being dosed.

Preferably, the switching mechanism comprises a disengaging structure which disengages the first thread arrangement of the rod element from the second thread arrangement of the dial shell upon changing the medical delivery device from the dosing status to the delivery status. Disengaging the first thread arrangement from the second thread arrangement it can be achieved that the rod element is axially moved without being rotated around the longitudinal axis of its stem. Thus, the rod element can be transferred by an axial force without any rotational movement. The rod element can be, by means of the disengaging structure, in a comparably simple construction embodied to allow the rod element to be axially moved by rotating it in the dosing status and by pushing it in the delivery status. Like this, the medical delivery device can efficiently be equipped with the features allowing operation in the two separated statuses or modes of operation.

Thereby, the disengaging structure of the switching mechanism preferably comprises a projection arranged at the first thread arrangement and a guidance groove into which the projection extends, wherein upon changing the medical delivery device from the dosing status to the delivery status the guidance groove is moved and the projection travels along the guidance groove such that the first thread arrangement disengages the second thread arrangement of the dial shell. The projection can extend in an essentially axial direction. The projection together with the guidance groove allow for efficiently disengaging the first thread arrangement from the second thread arrangement upon a switching the medical delivery device from the dosing status to the delivery status. In particular, such arrangement allows for an efficient and comparably simple mechanical implementation of the switching mechanism.

Thereby, the projection of the disengaging structure preferably axially extends and the guidance groove runs in a plane essentially perpendicular to the longitudinal axis of the stem of the rod element, wherein the guidance groove is shaped such that the projections are moved towards the longitudinal axis of the stem of the rod element when the guidance groove is rotated around the longitudinal axis of the stem of the rod element. In this connection, the term "axially extend" can relate to an extension in the direction or along the longitudinal axis of the stem of the rod element. By moving the first thread arrangement towards the longitudinal axis it can disengage the second thread arrangement. Accordingly it can be achieved that the rod element is no longer linked to the dial shell. Thus, the rod element is free to be axially moved by an axial force wherein rotating the dial shell does not forward the rod element anymore.

Preferably, a thread of the first thread arrangement of the rod element or of the second thread arrangement of the dial shell is equipped with a plurality of irregularities being positioned in a fixed distance to each other such that when rotating the dial shell around the longitudinal axis of the rod element the first thread arrangement of the rod element and the second thread arrangement of the dial shell engage at one of the plurality of irregularities at a predefined rotating angle. The irregularities can induce an audible and/or tactile signal each time the first thread arrangement and the second thread arrangement pass by a certain rotation. The irregularities can, e.g., be gaps in the walls of the thread.

Thereby, the irregularities are located such that rotating the dial shell about the predefined rotating angle causes the dosage chamber to change by a predefined volume. Particularly, each rotation about the predefined angle can change the volume of the dosage chamber by the same predefined amount. Like this a clear signal can be provided to a user of the medical delivery device during dosing indicating that the dosage volume has been changed by the predefined amount.

Preferably, the rod element comprises a stopper at its proximal end side. In particular the stopper can be located at a proximal end side of the stem of the rod element. The term "stopper" in this context can relate to a stopper in the narrow sense, i.e. a plug-like sealing member. It can also relate to alternative sealing members such as O-rings mounted to the stem or the like. The stopper can be made of an elastic material such as a rubber in order to comply providing tightness. By means of the stopper the rod element can tightly be arranged in a respective barrel body. Like this, an underpressure, partial vacuum or vacuum can be induced in the dosage chamber which allows for withdrawing liquid into the dosage chamber.

Preferably, the rod element comprises a transfer channel which extends through the stem along the longitudinal axis of its stem. It can further also extend through the stopper. The transfer channel allows for establishing a connection through the rod element and particularly axially through the stem thereof. It can be embodied as a transfer needle. In particular, a container arranged at or near the distal end of the rod element can be connected to the dosage chamber via the transfer channel. The transfer channel allows for transferring a liquid from the container through the rod element into the dosage chamber when the dial shell is rotated around the longitudinal axis. More specifically, by rotating the dial shell the rod element is moved along the longitudinal axis such that the dosage chamber is enlarged or reduced and liquid is transferred from the container into the dosage chamber or vice versa.

Preferably, the medical delivery device comprises a container seat connected to the distal end of the stem of the rod element. Such a container seat allows for connecting a container at a well-defined position and orientation. This allows for an efficient coupling of the container to the system.

Thereby, the transfer channel preferably comprises a tip and an opening wherein, in the dosing status of the medical delivery device, the tip and the opening project into the container seat such that they are located inside a container when the container is arranged in the container seat. The transfer channel can be a transfer needle. The container can be closed by a penetrable cover such as a septum, a cap or the like. By means of the transfer channel an axial connection of the container to the rod element is possible and it can be linearly coupled to the dosage chamber which allows for an efficient implementation.

Thereby, the transfer channel of the rod element preferably is closed upon changing the medical delivery device from the dosing status to the delivery status. The container seat preferably is axially moved in relation to the transfer channel upon changing the medical delivery device from the dosing status to the delivery status such that the opening of the transfer channel is sealed. Thereby, for sealing the transfer channel, the opening can be closed by embedding it in the closure of the container. For example, when the container is closed by a rubber plug or a septum, arranging the opening in the rubber plug or septum allows for tightly closing it by axially moving the container. For more efficiently allowing the tip to be sealed by the axially moved container, the opening of the tip can be embodied in a side wall of the tip rather than at its sharp end.

Preferably, the transfer channel connects the container seat with the dosage chamber such that, when a container with a fluid is arranged in the container seat and the rod element is moved along the longitudinal axis of its stem relative to the delivery orifice by rotating the dial shell around the stem of the rod element in a first direction of rotation, the fluid is transferred from the container to the dosage chamber. This allows for an efficient design of the delivery device.

Thereby, the dial shell and the transfer channel preferably are arranged such that, when the container is arranged in the container seat and the rod element is moved along the longitudinal axis of its stem relative to the delivery orifice by rotating the dial shell around the stem of the rod element in a second direction of rotation opposite to the first direction of rotation, the fluid is transferred from the dosage chamber to the container. This allows for a increasing as well as decreasing dose selection. The dosage in the dosing chamber can, thus, conveniently be varied, adjusted and corrected back and forth until a precise amount of liquid is dosed. After switching the medical delivery device to the delivery status no further dosing or adjustment is possible.

Preferably, the medical delivery device comprises a counter coupled to the rod element such that the counter indicates a volume of the dosage chamber formed by the rod element when being moved along the longitudinal axis of its stem relative to the delivery orifice by rotating the dial shell around the stem of the rod element. By coupling the counter to the rod element a movement of the latter in relation to the delivery orifice can be identified and directly reflected by adjusting the displayed number corresponding to the dosage volume or selected dose. Like this, an efficient implementation of a precise and purely mechanical dosage counter is possible.

Thereby, the counter preferably decouples from the rod element upon changing the medical delivery device from the dosing status to the delivery status. Like this, the selected dose volume can remain indicated during and after delivery. This allows for providing a purely mechanical marker to record the administered volume of liquid.

The first thread arrangement of the rod element and the second thread arrangement of the dial shell can comprise a thread and a male member. Thereby, in the dosing status, the male member can travel along the thread when rotating the dial shell around the stem of the rod element. The thread can be embodied as an outer thread on the stem of the rod element and the second thread arrangement can comprise a male member such as a pin extending into the outer thread. Preferably, the first thread arrangement of the rod element is a male thread arrangement with at least one male member projecting off the stem and the second thread arrangement of the dial shell comprises a thread for receiving the at least one male member. For projecting off the stem the at least one male member can radially or essentially radially extend from the stem such that it radially projects away from the stem. The at least one male member can be a pin. It can be fixedly arranged to or at the stem.

BRIEF DESCRIPTION OF THE DRAWINGS

The medical delivery device according to the invention is described in more detail hereinbelow by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
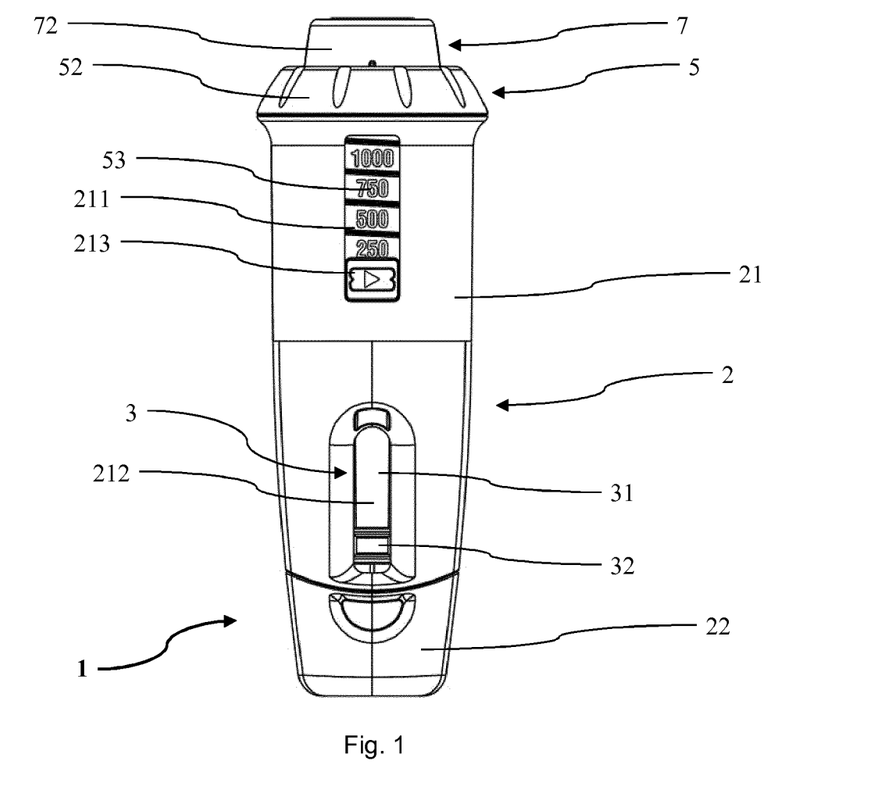
FIG. 1 shows a front view of a start position of an injection device as an embodiment of a medical delivery device according to the invention in a dosing status.

FIG. 1 shows an injection device 1 as an embodiment of a medical delivery device according to the invention in a dosing status. The injection device comprises a housing 2 with a body 21 and a needle shield 22. The body 21 has an interior, a top distal opening and a bottom proximal opening. It is further equipped with an indicator window 211 in an upper part and a chamber window 212 vertically below the indicator window.

In the interior of the body 21 a rod element 3 with a vertically aligned stem 31 and a rubber stopper 32 at the lower end of the stem 31 are arranged. The rubber stopper 32 and a lower part of the stem 31 are visible through the chamber window 212 of the body 21 of the housing 2.

Through the distal opening of the housing 2 a dosing activator 5 extends into the interior of the body 21. The dosing activator 5 comprises a gripping ring 52 which is positioned outside the housing 2 and which laterally overlaps the distal opening of the hosing 2. As explained in more detail below, the dosing activator 5 has a dosage marking 53 as part of a counter for indicating an amount or volume of a medicament dosed. In the start position shown in FIG. 1 no medicament is dosed such that no volume is indicated in a highlighting element 213 of the indicator window 211. Rather, an arrow indicating the direction of rotation for dosing, i.e. an anti-clockwise direction, is visible through the highlighting element 213 of the indicator window 211. The dosage marking 53 and the highlighting element together are comprised by the counter of the injection device 1.

Also through the distal opening of the housing 2 a switch activator 7 extends into the interior of the body 21 and into the dosing activator 5. The switch activator 7 comprises a gripping ring 72 which is positioned outside the housing 2 and the dosing activator 5.

Figure 2:
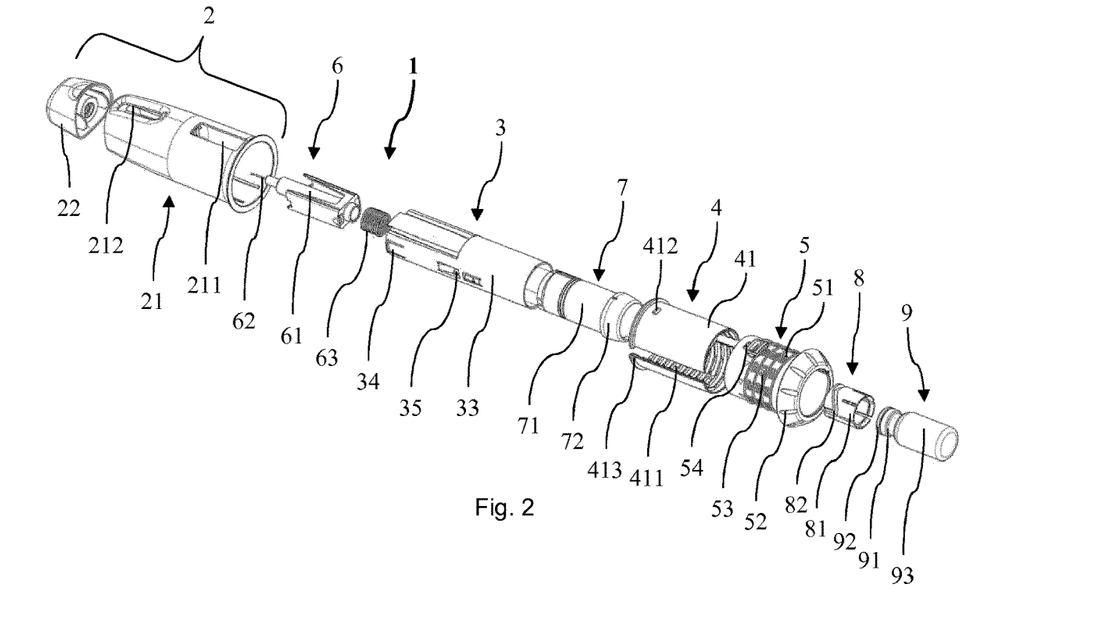
FIG. 2 shows a perspective exploded view of the injection device of FIG. 1.

In FIG. 2 the injection device 1 is shown in an exploded view such that single parts are visible. The injection device 1 is designed to receive a vial 9 as a container. In a common manner the vial 1 has a body 93 and a neck 91 which is closed by a cap 92. In the interior of the body 93 a liquid medicament is stored which is to transfer, dose and deliver or inject by means of the injection device 1.

The rod element 3 comprises a cylinder portion 33 which is sized to about half length of the rod element, i.e. the right hand half of it in FIG. 2. The cylinder portion 33 has a hollow interior dimensioned to receive a cylinder portion 71 of the switch activator 7. The switch activator 7 also essentially is cylindrical and has a hollow interior which is shaped to receive the vial 9 and a vial seat 8 as a container seat. The vial seat 8 has a neck holder 81 and a cylindrical outer surface provided with a hub groove 82.

The rod element 3 is equipped with two opposite pins 35 as male members of an outer or first thread arrangement. The pins 35 radially project off the rest of the rod element 3. The pins 35 are to a certain extent flexibly mounted in order to allow to be forced inwardly, i.e. into the direction of a longitudinal axis of the rod element 3. The rod element 3 further comprises two opposite limiting fins 34 positioned near a proximal end of the rod element 3.

The medical injection device 1 further comprises a dial shell 4 having two half-cylindrical clamshells 41. On the inner surfaces, both clamshells 41 are equipped with thread sections wherein the tread sections of the clamshells 41 are formed to build two parallel continuous threads 411 as inner or second thread arrangement when the clamshells 41 are put together forming a cylinder. At the proximal ends the clamshells 41 are provided with an outwardly extending flange 413. Further, each of the clamshells 41 is equipped with a rim segment 412 radially or outwardly projecting off the outer surface. The clamshells 41 are dimensioned to fit around the cylinder portion 33 of the rod element 3.

The dosing activator 5 has a cylindrical body 51 with a hollow interior, wherein the dosage marking 53 is provided at and around an outer surface of the cylindrical body 51. The gripping ring 52 forms a distal end of the dosing activator 5. In the cylindrical body 51 a pair of recesses 54 corresponding to the rim segments 412 of the clamshells 41 is arranged. The dosing activator 5 is dimensioned to be arranged around the clamshells 41 such that the rim segments 412 engage the recesses 54 and fix the dial shell 4 to the dosing activator 5 when being arranged around the cylinder portion 33 of the rod element 3.

Between the stem 31 of the rod element 3 and the proximal opening of the body 21 of the housing 2 a dosage member 6 is arranged. The dosage member 6 has a spring 63, a chamber cylinder 61 and a delivery needle 62 as a delivery orifice of the injection device 1. The chamber cylinder 61 is dimensioned such that the stem 31 and the rubber stopper 32 of the rod element 3 fit into it.

Figure 3:
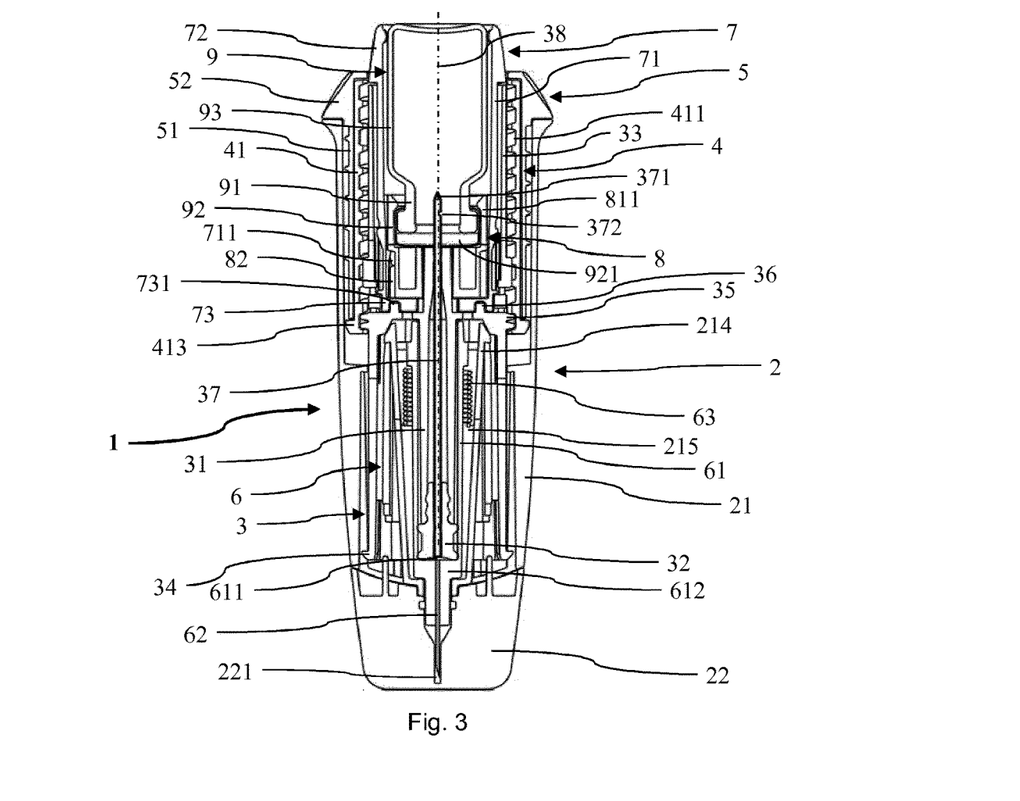
FIG. 3 shows a cross sectional view of the injection device of FIG. 1 in the dosing status while being in the start position.

FIG. 3 shows the assembled injection device 1 in the start position. The injection device 1 is presented in an upright alignment such that the proximal end is at the bottom and the distal end at the top. As described above, the switch activator 7 extends inside the hollow interior of the cylinder portion 33 of the rod element 3. Thereby, the cylinder portion 71 of the switch activator 7 is inside the rod element 3 and the grip portion 72 of the switch activator 7 upwardly projects out of the rod element 3. More particularly, the grip portion 71 of the switch activator 7 is dimensioned such that it does not fit into the cylinder portion 33 of the rod element 3 but abuts a distal opening thereof.

Inside the hollow interior of the switch activator 7 the vial seat 8 is positioned at a bottom 73 of the switch activator 7. A hub protrusion 711 inwardly projects from the inner surface of the cylinder portion 71 of the switch activator 7 into the direction of the vial seat 8. The hub protrusion 711 engages the hub groove 82 of the vial seat 8 such that the switch activator 7 and the vial seat 8 can interact as described in more detail below.

The rod element 3 has a central longitudinal axis 38 which in FIG. 3 vertically extends. The longitudinal axis 38 of the rod element 3 corresponds to longitudinal axes of the housing 2, the dial shell 4, the dosing activator 5, the dosage member 6, the switch activator 7, the vial seat 8, the vial 9 and the overall device 1.

The rod element 3 further has a transfer needle 37 which centrally passes through the stem 31 and the rubber stopper 32. The stem 31 upwardly extends into the interior of the cylinder portion 33 and into the vial seat 8. Thereby, the stem 31 is torque resistantly connected to the vial seat 8 by interacting form-fitting parts. The transfer needle 37 extends from a bottom or proximal end of the rubber stopper 32 axially through the rubber stopper 32 and the stem 31 and projects above the top or distal end of the stem 31 ending in a sharp tip 371. Downwardly, the stem 31 extends into the chamber cylinder 61 of the dosage member 6.

The rubber stopper 32 is contained by the stem 31 such that it is arranged at the bottom or proximal end of the stem 31. Thus, the rubber stopper 32 is located fully inside the chamber cylinder 61 of the dosage member 6 wherein, in the start position shown in FIG. 3, the rubber stopper 32 abuts a bottom 612 of the chamber cylinder 61. The proximal end of the rubber stopper 32 is concave such that between the rubber stopper 32 and the bottom 612 of the chamber cylinder 61 a minimal dosage chamber 611 is formed inside the chamber cylinder 61. The bottom 612 of the chamber cylinder 61 has a downwardly extending post and is provided with the delivery needle 62 which projects through the post. The bottom or proximal end of the delivery needle 62 is received in a seal channel 221 of the needle shield 22 of the housing such that the delivery needle 62 is covered, protected and sealed.

The neck holder 81 of the vial seat 8 has a retaining formation 811 which comprises vertical slits and an inwardly extending flange end. In a step of preparing the injection device 1, the vial 9 is pressed top down into the switch activator 7 and the vial seat 8. Thereby, the vertical slits allow the retaining formation 811 to be sufficiently moved in an outward direction such that a head of the vial 9 with the cap 92 passes the flange end of the retaining formation 811. Once the vial 9 is sufficiently pressed down, the flange end of the retaining formation 811 snaps behind the head and in the neck 91 of the vial 9 such that the vial 9 is held. In this way, the vial 9 is vertically mounted top down in the injection device 1 with its cap 92 abutting the distal end of the stem 31 of the rod element 3. At the top distal opening of the switch activator 7 a bulge inwardly projects which fits and guides the exterior of the body 93 of the vial 9.

While the vial 9 being pressed into the vial seat 8 the tip 371 of the transfer needle 37 penetrates the cap 92 including a septum 921. The tip 371 forms the top or distal end of the transfer needle 37. When the vial 9 is completely retained in the vial seat 8 the transfer needle 37 extends into the interior of the vial 9. Close to the tip 371 but slightly below it a sideward opening 372 is provided in the transfer needle 37. In the start position shown in FIG. 3, the transfer needle 37 forms an open duct as transfer channel between the interior of the vial 9 and the dosage chamber 611 of the dosage member 6.

The pins 35 of the outer thread arrangement of the rod element 3 horizontally project from the rest of the rod element 3 to the left and to the right into the inner threads 411 of the dial shell 4 formed by the two clamshells 41. Thereby, each of the pins 35 engages one of the two inner threads 411. The outer thread arrangement of the rod element 3 further comprises two projections 36 of a disengaging structure of a switching mechanism which are located close to the pins 35 and which axially extend into an upward direction. Each of the projections 36 engages a guidance groove 731 of the disengaging structure of the switching mechanism embodied in the bottom 73 of the switch activator 7. The guidance grooves 73 run in a plane perpendicular to the longitudinal axis 38 of the stem 31 of the rod element 3. They helically extend on the bottom 73 and are continuously approaching a centre of the bottom 73.

The body 21 of the housing 2 further comprises a bottom 213 with an opening through which the post of the bottom 612 of the chamber cylinder 61 of the dosage member 6 extends into the needle shield 22. From the bottom 213 of the body 21 two retaining arms 214 and a spring rest 215 upwardly extend into the interior of the body 23. Thereby, the two retaining arms 214 are snapped behind a corresponding skirt of the dosage member 6. The helical spring 63 is clamped between the spring rest 215 and a horizontal surface of the dosage member 6. Thus, the dosage member 6 is connected to the body 21 of the housing 2 by the retaining arms 214 wherein the spring 63 is pre-stressed between the body 21 and the dosage member 6.

Figure 4:
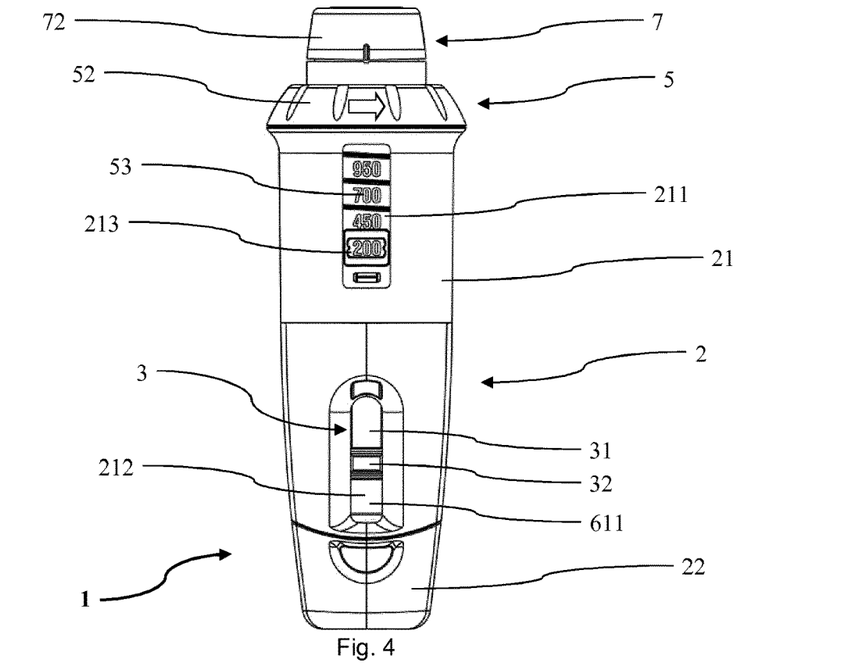
FIG. 4 shows a front view of the injection device of FIG. 1 in the dosing status after dosing.
Figure 5:
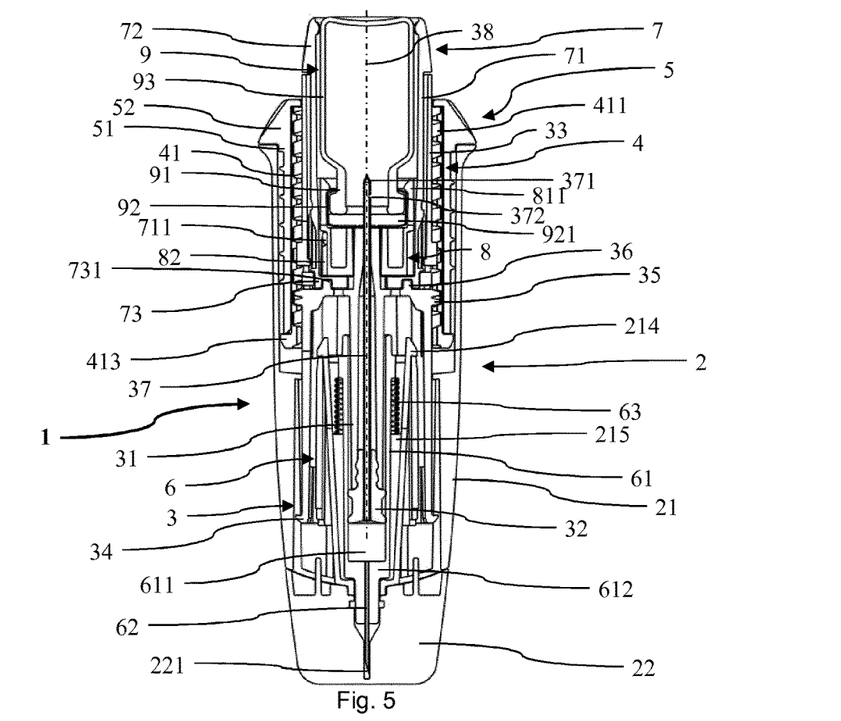
FIG. 5 shows a cross sectional view of the injection device of FIG. 4.

FIG. 4 and FIG. 5 show the injection device 1 after dosing, i.e. after transferring 200 μl of the medicament from the vial 9 into the dosage chamber 611. As indicated by the arrow in FIG. 4, for dosing the dosing activator 5 is rotated anti-clockwise relative to the housing 2. Thereby, the housing 2 can be held at its body 21 by one hand of a patient and with the other hand the patient can rotate the gripping ring 52 of the dosing activator 5 relative to the housing 2. Since the clamshells 41 of the dial shell 4 are connected to the dosing activator 5 in a torque-resistant manner by the rim segments 412 projecting into the recesses 54, the dial shell 4 is rotated together with the dosing activator 5. In the meantime the rod element 3 is torque-resistantly connected to the housing 2 via the dosage member 6 and the retaining arms 214 of the housing 2 such that it is non-rotatable about its axis 38. Thus, the dial shell 4 rotates around the rod element 3 causing the pins 35 to travel along the threads 411. Like this, the rod element 3 is upwardly moved along the longitudinal axis 38 of the stem 31.

When axially moving the rod element 3 in an upward direction, the dosing chamber 611 between the rubber stopper 32 and the bottom of the chamber cylinder 61 of the dosage member 6 increases. In the meantime, an underpressure or partial vacuum is created in the dosing chamber 61 such that the medicament is drawn from the vial 9 through the transfer needle 37 into the dosing chamber 611. The threads 411 of the dial shell 4 are provided with small gaps as irregularities. The gaps are distributed along the threads 411 such that the pins 35 travelling between two adjacent gaps causes the dosage chamber 611 to change by a predefined volume, e.g. of 25 μl. When the pins pass one of the gaps of the threads 411 a click signal is induced which can be heard and felt. Thus, when the patient rotates the dosing activator 5 and notices a click they know that the dosed volume of medicament has changed, e.g. by 25 μl.

When the dosing activator 5 rotates relative to the housing 2 during dosing, the number visible in the highlighting element 213 of the indicator window 211 changes in correspondence with the medicament volume in the dosing chamber 611. More particularly, the highlighting element 213 is on one hand guided in the indicator window 211 such that it is axially or vertically movable relative to the body 21 of the housing 2 but not tangentially. On the other hand the outer surface of the body 51 of the dosing activator 5 is provided with a thread rib which is connected to the highlighting element 213 via a corresponding groove. Thus, when the dosing activator 5 rotates relative to the housing 2, the highlighting element 213 is vertically moved by the thread rib interacting with groove. Compared to FIG. 1 in which the highlighting element 213 is at the bottom end of the indicator window 211, in FIG. 4 it is upwardly moved and lies over the numeral 200 of the dosage marking. This indicates that 200 μl of the medicament is transferred into the dosage chamber 611.

When being in the dosing status or mode, the dosing activator 5 can be rotated in both directions. Thereby, an anti-clockwise rotation causes the dosage volume 611 to increase and, vice versa, a clockwise rotation causes the dosage volume 611 to decrease such that the medicament is transferred back to the vial 9.

Figure 6:
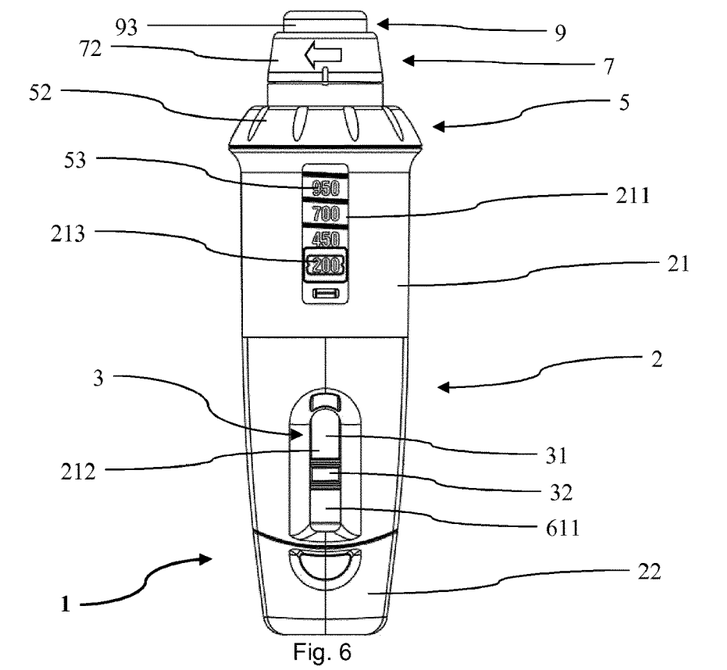
FIG. 6 shows a front view of the injection device of FIG. 1 after being switched from the dosing status to a delivery status.
Figure 7:
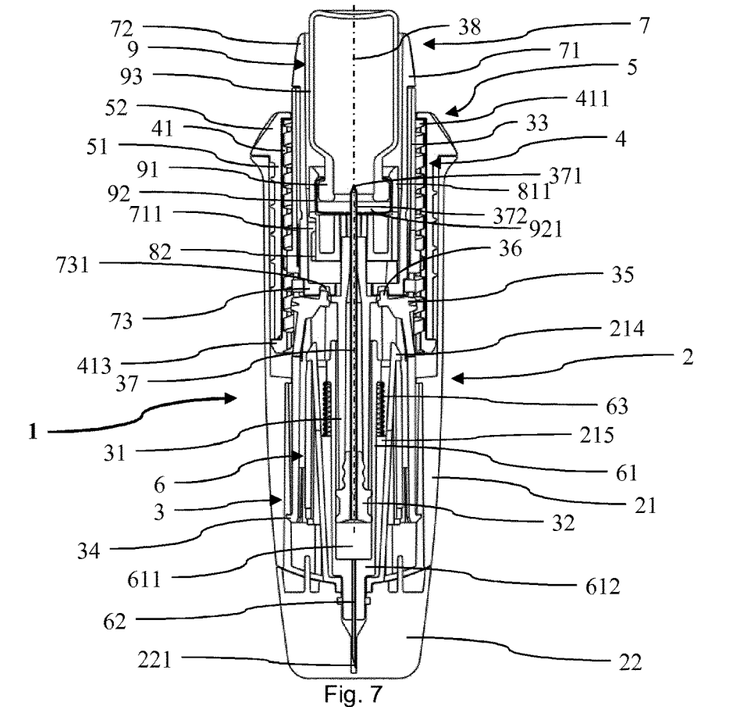
FIG. 7 shows a cross sectional view of the injection device of FIG. 6.

In FIG. 6 and FIG. 7 the injection device 1 is shown after being switched from the dosing status or mode into the delivery status. As indicated by the arrow in FIG. 6, for switching the switch activator 7 is rotated clockwise relative to the housing 2 and relative to the rod element 3 connected to the housing 2 as described above. Thereby, the housing 2 can again be held at its body 21 by one hand of the patient and with the other hand the patient can rotate the gripping ring 72 of the switch activator 7 relative to the housing 2.

Since the guidance groove 731 at the bottom 73 of the switch activator 7 helically extends and continuously approaches the centre of the bottom 73, the projections 36 of the outer thread arrangement are moved towards the axis 38 when the switch activator 7 is rotated and, concomitantly, the projections 36 travel along the guidance groove 731. Together with the projections 36 the complete arms including the pins 35 are move towards the longitudinal axis 38 such that the pins 35 disengage the threads 411 of the dial shell 4 wherein, in the delivery status shown in FIG. 7, the pins 35 are completely disengaged from the threads 411. Thereby, the rotation of the dosing activator 5 does no longer move the rod element 3 and the axial movement of the rod element 3 is no longer prevented by the pins 35.

Furthermore, since the container seat 8 is torque-resistantly connected to the rod element 3, the switch activator 7 is also rotated about the vial seat 8. In particular, the cylinder portion 71 together with its hub protrusion 711 rotates about the vial seat 8. Thereby, the hub protrusion 711 travels along the hub groove 82 of the vial seat 8 wherein, due to the design of the hub groove 82, the vial seat 82 together with the vial 9 is lifted. In the position shown in FIG. 6 and FIG. 7 the vial 9 is axially lifted to such an extent that the septum 921 of the cap 92 of the vial 9 covers the sideward opening 372 of the transfer needle 37 of the rod element 3. Like this, the transfer needle 37 is sealed and the duct between the vial 9 and the dosage chamber 611 is safely closed. Thus, no transfer of medicament is possible between the vial 9 and the dosage chamber 611.

Figure 8:
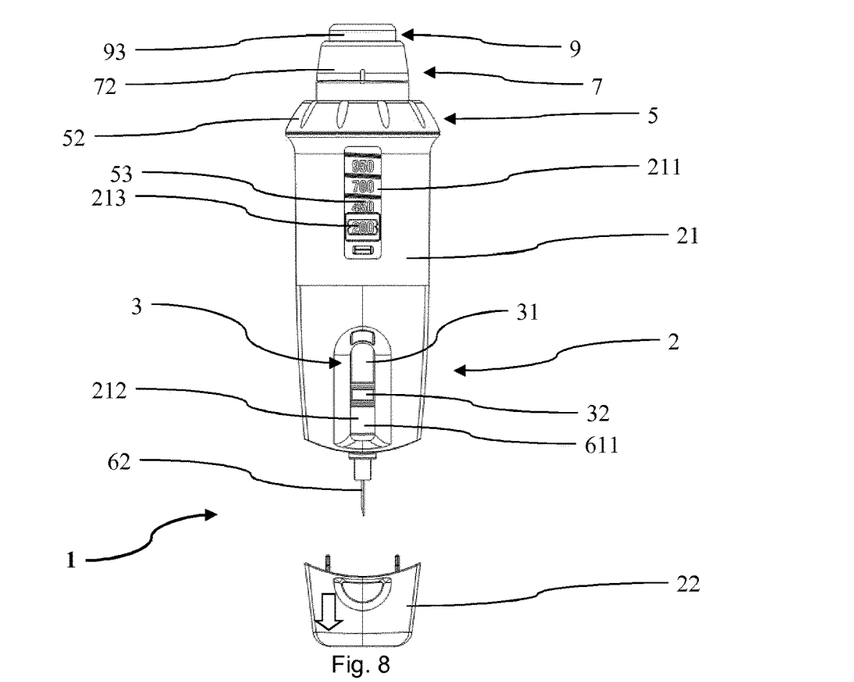
FIG. 8 shows a front view of the injection device of FIG. 1 in the delivery status after removal of the needle shield.
Figure 9:
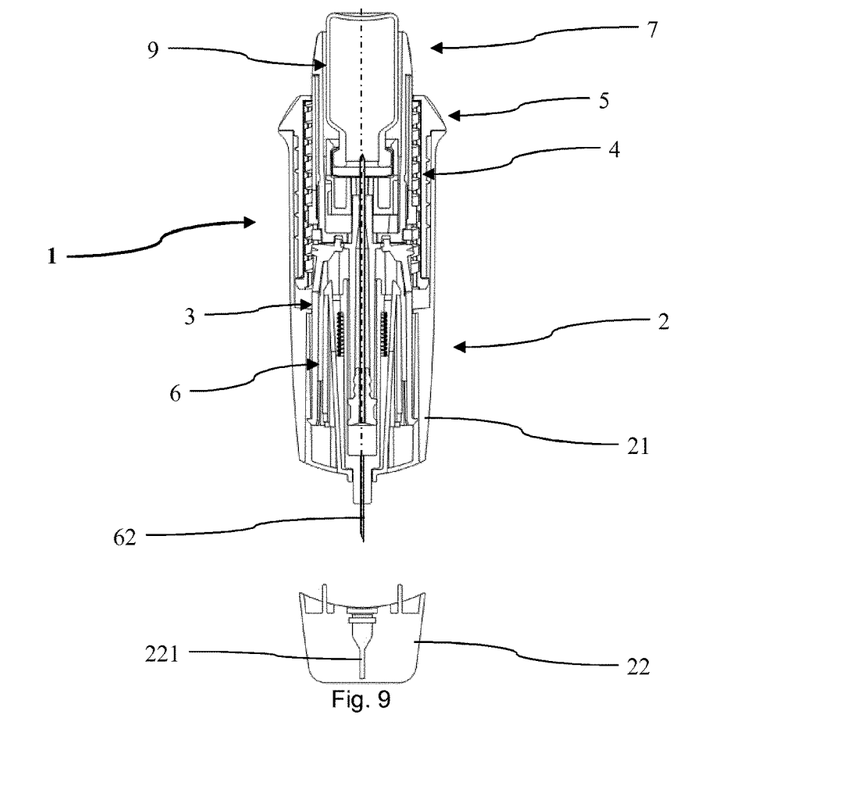
FIG. 9 shows a cross sectional view of the injection device of FIG. 8.

FIG. 8 and FIG. 9 show the injection device 1 in its delivery status ready to inject the medicament. As indicated by the arrow in FIG. 8, the needle shield 22 is downwardly pulled off the body 21 of the housing 2. Thereby, the delivery needle 62 is exposed and ready for delivery.

Figure 10:
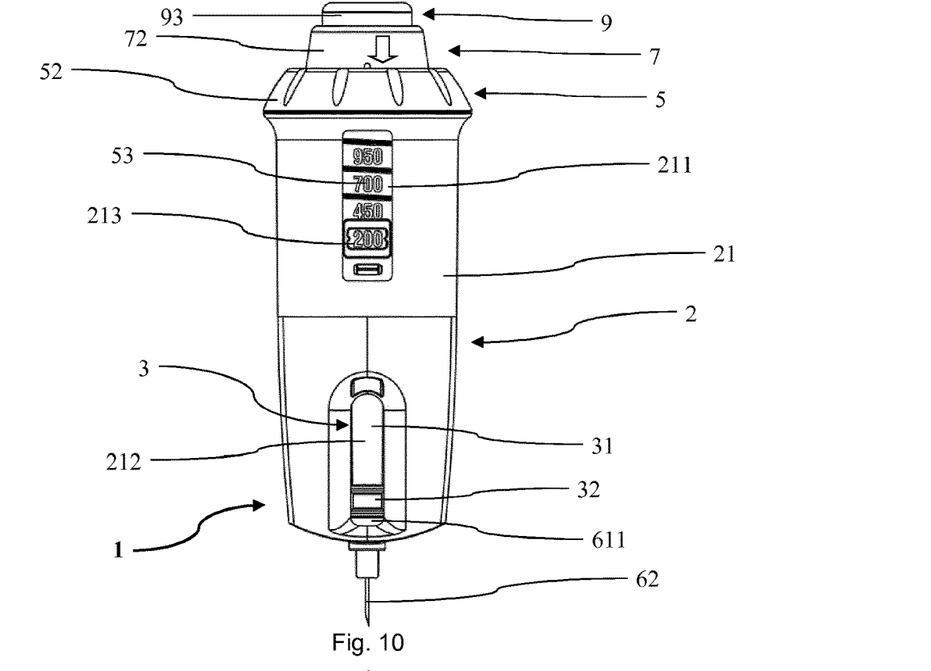
FIG. 10 shows a front view of the injection device of FIG. 1 in the delivery status after delivery.
Figure 11:
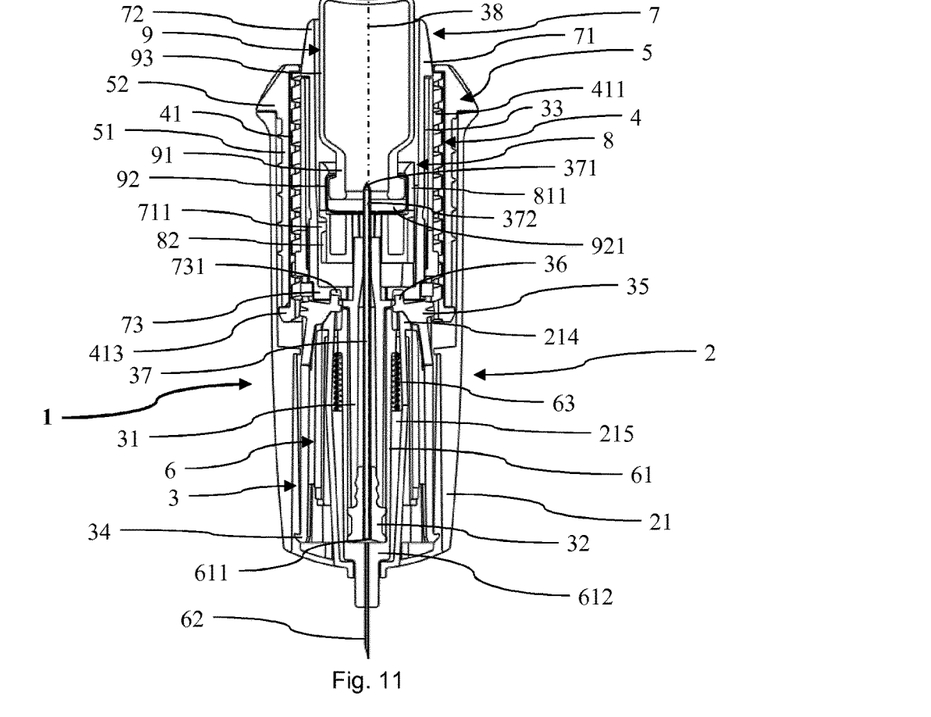
FIG. 11 shows a cross sectional view of the injection device of FIG. 10.

In FIG. 10 and FIG. 11 the injection device 1 is shown in its delivery status after injection. As indicated by the arrow in FIG. 10 the switch activator is moved downwardly. More particularly, for delivering the medicament an axial force is applied on the vial 9 which upwardly extends out of the switch activator 7. For example, such axial force can be provided by a thumb of a hand of the patient wherein the housing 2 is held by the patient. During delivery, the axial force is transmitted from the vial 9 via the vial seat 8 to the rod element 3 such that its rubber stopper 32 is pressed into the dosage chamber 611 and the medicament is supplied out of the needle 62. After delivery, as shown in FIG. 11, the volume of the dosage chamber 611 is minimized such that the medicament is essentially completely delivered.

Figure 12:
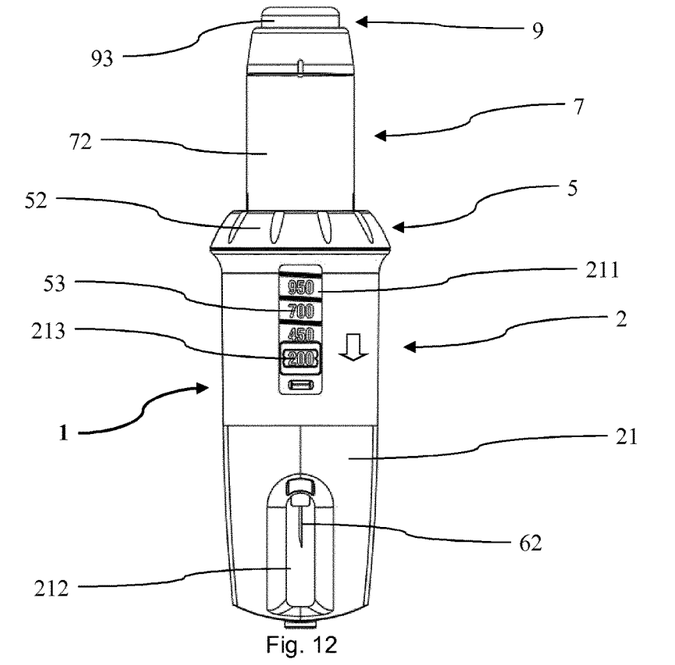
FIG. 12 shows a front view of the injection device of FIG. 1 in the delivery status after a needle being covered and protected.
Figure 13:
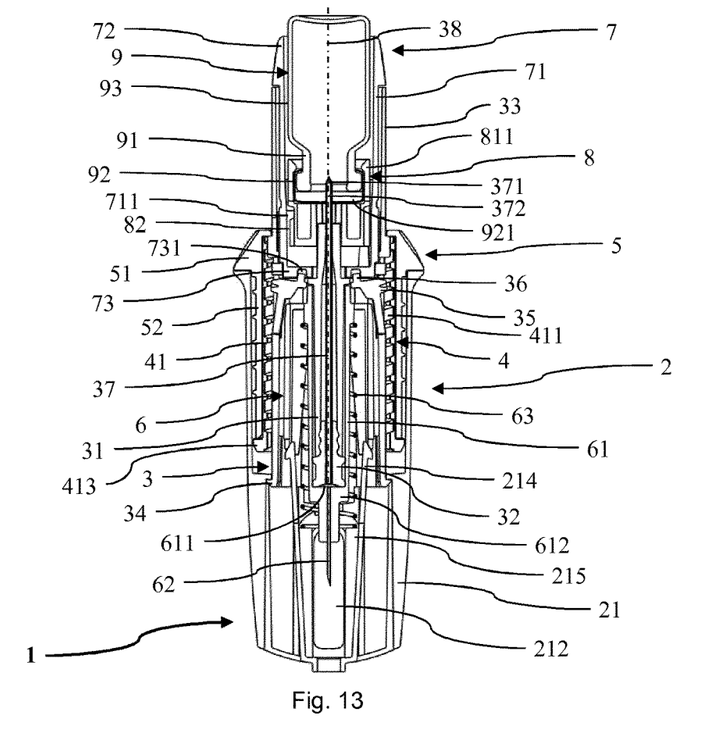
FIG. 13 shows a cross sectional view of the injection device of FIG. 12.

Additionally, while axially moving the rod element 3 in a downward direction, the retaining arms 214 are pressed inwardly into the direction of the axis 38. After injection, the retaining arms 214 are completely disengaged from the corresponding skirt of the dosage member 6 such that the housing 2 and the dosage member are disconnected from each other. As shown in FIG. 12 and FIG. 13 this allows the spring force of the spring 63 initially being pre-stressed between the spring rest 215 of the body 21 of the housing 2 and the horizontal surface of the dosage member 6 to axially move the body 21 in relation to the other parts of the injection device 1 and particularly also in relation to the needle 62. Like this, the needle 62 is completely covered by the body 21 which can prevent stick injuries by the needle 62 after delivery of the medicament.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A medical delivery device, comprising:
a rod element having a stem with a longitudinal axis, a first thread arrangement, a proximal end and a distal end;
a dial shell having a second thread arrangement;
a delivery orifice arranged adjacent to the proximal end of the stem of the rod element; and
a switching mechanism for changing the medical delivery device from a dosing status to a delivery status, the switching mechanism including a disengaging structure,
wherein, in the dosing status of the medical delivery device,
the first thread arrangement of the rod element and the second thread arrangement of the dial shell engage, and
the rod element is movable along the longitudinal axis of its stem relative to the delivery orifice by rotating the dial shell around the stem of the rod element causing the first thread arrangement of the rod element and the second thread arrangement of the dial shell to travel along each other, wherein a dosage chamber is formed between the rod element and the delivery orifice which dosage chamber increases when the rod element moves away from the delivery orifice, and
moving the rod element along the longitudinal axis of its stem by applying an axial force to the rod element is prevented by the engagement between the first thread arrangement of the rod element and the second thread arrangement of the dial shell, and
wherein, in the delivery status of the medical delivery device,
the rod element is movable along the longitudinal axis of its stem relative to the delivery orifice by applying an axial force to the rod element, and
moving the rod element along the longitudinal axis of its stem by rotating the dial shell around the stem of the rod element is prevented by the disengaging structure of the switching mechanism which disengages the first thread arrangement of the rod element from the second thread arrangement of the dial shell upon changing the medical delivery device from the dosing status to the delivery status.

2. The medical delivery device according to claim 1, wherein the disengaging structure of the switching mechanism comprises a projection arranged at the first thread arrangement of the rod element and a guidance groove into which the projection extends, wherein upon changing the medical delivery device from the dosing status to the delivery status the guidance groove moved and the projection travels along the guidance groove such that the first thread arrangement of the rod element disengages the second thread arrangement of the dial shell.

3. The medical delivery device according to claim 2, wherein the projection of the disengaging structure axially extends and the guidance groove runs in a plane essentially perpendicular to the longitudinal axis of the stem of the rod element, wherein the guidance groove is shaped such that the projection is moved towards the longitudinal axis of the stem of the rod element—when the guidance groove is rotated around the longitudinal axis of the stem of the rod element.

4. The medical delivery device according to claim 1, wherein a thread of the first thread arrangement of the rod element and/or of the second thread arrangement of the dial shell is equipped with a plurality of irregularities being positioned in a fixed distance to each other such that when rotating the dial shell around the longitudinal axis of the rod element the first thread arrangement of the rod element and the second thread arrangement of the dial shell interact with one of the plurality of irregularities at a predefined rotating angle.

5. The medical delivery device according to claim 4, wherein the irregularities are located such that rotating the dial shell about the predefined rotating angle causes the dosage chamber to change by a predefined volume.

6. The medical delivery device according to claim 1, wherein the rod element comprises a transfer channel which extends through the stem along the longitudinal axis of the stem.

7. The medical delivery device according to claim 6, comprising a container seat connected to the distal end of the stem of the rod element.

8. The medical delivery device according to claim 7, wherein the transfer channel comprises a tip and an opening wherein, in the dosing status of the medical delivery device, the tip and the opening project into the container seat such that they extend into a container when the container is arranged in the container seat.

9. The medical delivery device according to claim 8, wherein the transfer channel of the rod element is shut upon changing the medical delivery device from the dosing status to the delivery status.

10. The medical delivery device according to claim 9, wherein the container seat is axially moved in relation to the transfer channel upon changing the medical delivery device from the dosing status to the delivery status such that the opening of the transfer channel is sealed.

11. The medical delivery device according to claim 7, wherein the transfer channel connects the container seat with the dosage chamber such that, when a container with a fluid is arranged in the container seat and the rod element is moved along the longitudinal axis of its relative to the delivery orifice by rotating the dial shell around the stem of the rod element in a first direction of rotation, the fluid is transferred from the container to the dosage chamber.

12. The medical delivery device according to claim 11, wherein the dial shell and the transfer channel are arranged such that, when the container is arranged in the container seat and the rod element is moved along the longitudinal axis of its stem relative to the delivery orifice by rotating the dial shell around the stem of the rod element in a second direction of rotation opposite to the first direction of rotation, the fluid is transferred from the dosage chamber to the container.

13. The medical delivery device according to claim 1, comprising a counter coupled to the rod element such that the counter indicates a volume of the dosage chamber formed by the rod element when being moved along the longitudinal axis of its stem relative to the delivery orifice by rotating the dial shell around the stem of the rod element.

14. The medical delivery device according to claim 13, wherein the counter decouples from the rod element upon changing the medical delivery device from the dosing status to the delivery status.

15. The medical delivery device according to claim 1, wherein the first thread arrangement of the rod element is a male thread arrangement with at least one male member projecting off the stem and the second thread arrangement of the dial shell comprises a thread for receiving the at least one male member.

* * * * *